(12) United States Patent
Drain et al.

(10) Patent No.: US 6,460,406 B1
(45) Date of Patent: Oct. 8, 2002

(54) CELL FOR MEASURING A LIQUID ACTIVITY, PROVIDED WITH PROBE RINSING MEANS

(75) Inventors: François Drain, Breteche; Christian Trevisan, Chatou, both of (FR)

(73) Assignee: Compagnie Generale des Matieres Nucleaires, Velizy Villacoublay (FR)

( * ) Notice: Subject to any disclaimer, the term of this patent is extended or adjusted under 35 U.S.C. 154(b) by 0 days.

(21) Appl. No.: 09/582,979

(22) PCT Filed: Nov. 9, 1999

(86) PCT No.: PCT/FR99/02742

§ 371 (c)(1),
(2), (4) Date: Jul. 7, 2000

(87) PCT Pub. No.: WO00/28308

PCT Pub. Date: May 18, 2000

(30) Foreign Application Priority Data

Nov. 10, 1998 (FR) .............................................. 98 14142

(51) Int. Cl.[7] .............................. B01L 3/00; B01L 9/04; G01N 21/15
(52) U.S. Cl. ................ 73/53.01; 73/864.21; 73/864.32; 356/440; 422/102
(58) Field of Search ............................. 73/53.01, 54.01, 73/864.21, 864.32, 863.82; 250/576; 356/440, 342; 422/102

(56) References Cited

U.S. PATENT DOCUMENTS

| 2,641,127 | A | * | 6/1953 | Kerr et al. ....................... 73/53 |
| 2,760,832 | A | * | 8/1956 | Bidwell ........................... 308/9 |
| 3,025,464 | A | * | 3/1962 | Bond ............................. 324/61 |
| 3,071,962 | A | * | 1/1963 | Perkins, Jr. ..................... 73/59 |
| 3,313,145 | A | * | 4/1967 | Kraynik et al. .................. 73/54 |
| 3,765,226 | A | * | 10/1973 | Strickland et al. .............. 73/53 |
| 3,777,549 | A | * | 12/1973 | Lodge ........................... 73/53 |
| 4,151,744 | A | * | 5/1979 | Hemmings ...................... 73/54 |
| 4,661,845 | A | | 4/1987 | Saito et al. .................... 358/99 |
| 4,840,137 | A | * | 6/1989 | Beauvais et al. ............. 116/227 |
| 4,874,243 | A | | 10/1989 | Perren ......................... 356/342 |
| 4,933,886 | A | * | 6/1990 | George ......................... 364/556 |
| 4,946,651 | A | * | 8/1990 | Liston et al. ................ 422/102 |
| 4,946,652 | A | | 8/1990 | Dewald et al. ............. 422/104 |

FOREIGN PATENT DOCUMENTS

DE      34 46 908 A     7/1985

* cited by examiner

Primary Examiner—Hezron Williams
Assistant Examiner—David J. Wiggins
(74) Attorney, Agent, or Firm—Pearne & Gordon LLP

(57) ABSTRACT

The liquid to be measured flows through a flow-pipe and bathes the end (1) of a pivoting probe in a spectrophotometric cell (2). One measuring surface (15) of the probe (2) remains immersed in the liquid whose level is advantageously assured by an overflow barrier (19); but when the probe has pivoted, the measuring surface opens onto a duct (23) in which a rinsing liquid flows and leads into the flow-pipe and cleans it. This rinsing is quick and safe and requires no dismounting of the probe. The invention applies in particular to liquids containing radioactive products such as uranium and/or plutonium.

5 Claims, 5 Drawing Sheets

CELL FOR MEASURING A LIQUID ACTIVITY, PROVIDED WITH PROBE RINSING MEANS

The invention relates to a cell for measuring the activity of a liquid.

Spectrophotometric cells are routinely used to measure concentrations of uranium and plutonium for example in radioactive liquids. They comprise one end called an optode which is immersed in the liquid containing radioactive elements, a spectrophotometer which is placed in a zone accessible to operators and which measures the concentrations of the elements and displays results, and an optic fibre which connects the spectrophotometer to the optode.

An optode is generally made of a quartz cylinder through which pass two parallel branches of the optic fibre allocated to out and return travel of the light by means of a reflection produced in the bottom part of the optode. A slit is cut in the quartz cylinder to interrupt the fibre over part of its length belonging to the return branch or both branches; this length is called the "optic distance" and serves to collect the photons emitted by the active particles in the liquid for measurement purposes. It is therefore essential that the optic distance must be fully immersed in the liquid to be measured.

At the present time, measurements consist of immersing the optode in a beaker containing a sample of liquid to be analysed, which requires certain manipulations. Other manipulations are required before each new use, since the optode must be rinsed then calibrated. The use of these spectrophotometric devices is therefore slow and tiresome, and requires precautionary measures to avoid contamination.

The measuring cell put forward here, which shall be described in detail below, offers the chief advantages of allowing direct, fast and safe measuring of a liquid without having to draw off a liquid sample from the circuit in which it is contained to pour it into a container, nor does it require complicated manipulations. Above all, it can allow easy rinsing and calibrating even though it is normally not accessible.

The concrete measures taken to achieve these advantages consisted of integrating the optode at the end of a probe, and of causing a portion of a flow circuit of the liquid to be measured to pass through the cell such that the optode is immersed in this portion of circuit. A rinsing circuit is added which leads to the optode so that it can be rinsed at will. The optode remains inserted in the cell but may be oriented either towards the liquid to be measured or towards the rinsing liquid.

To resume, the invention in its more general form concerns a cell for measuring the activity of a liquid, comprising a probe, the probe being equipped with a cylindrical measuring end, characterised in that it comprises a liquid flow-pipe provided with a cylindrical alveolus in which the cylindrical end is inserted, the alveolus opening on one side into the flow-pipe and being delimited on the other side by a wall, a clearance existing between the end of the probe and the wall; in addition, a rinsing liquid duct leads into the alveolus via the wall, and the probe is mounted so that it can pivot freely within the cell.

Immersion of the optode is guaranteed if an overflow barrier is placed downstream from the alveolus across the rinsing liquid duct.

A more detailed description follows in order to better apprehend its content, purposes and advantages by means of its preferred embodiment illustrated in the following figures.

Figure 3:
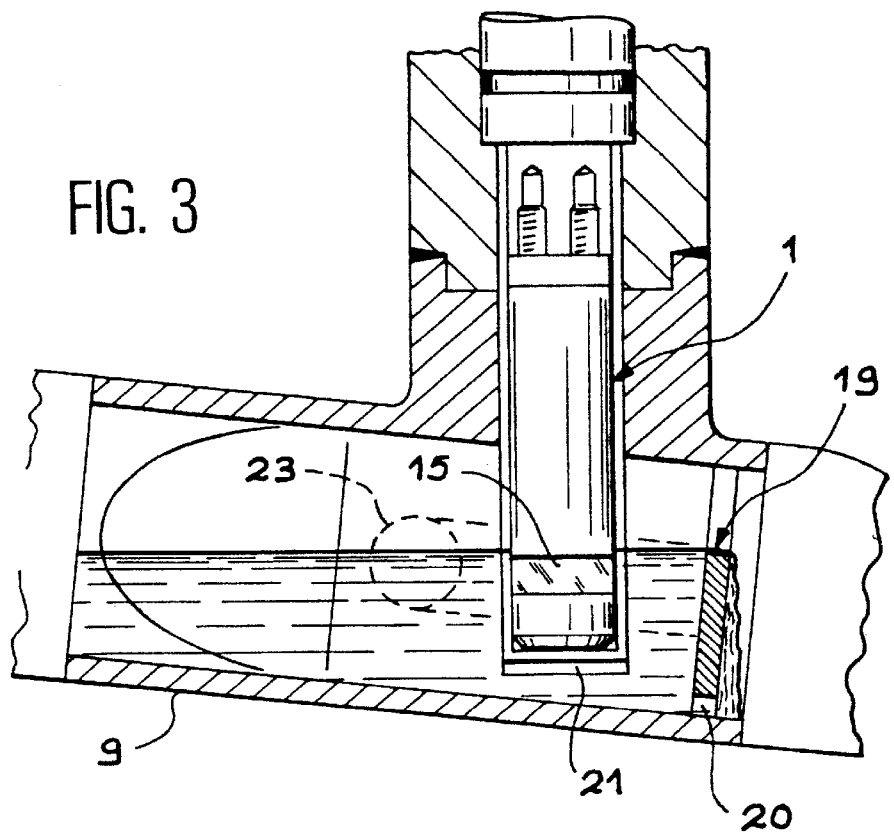
Figure 4:
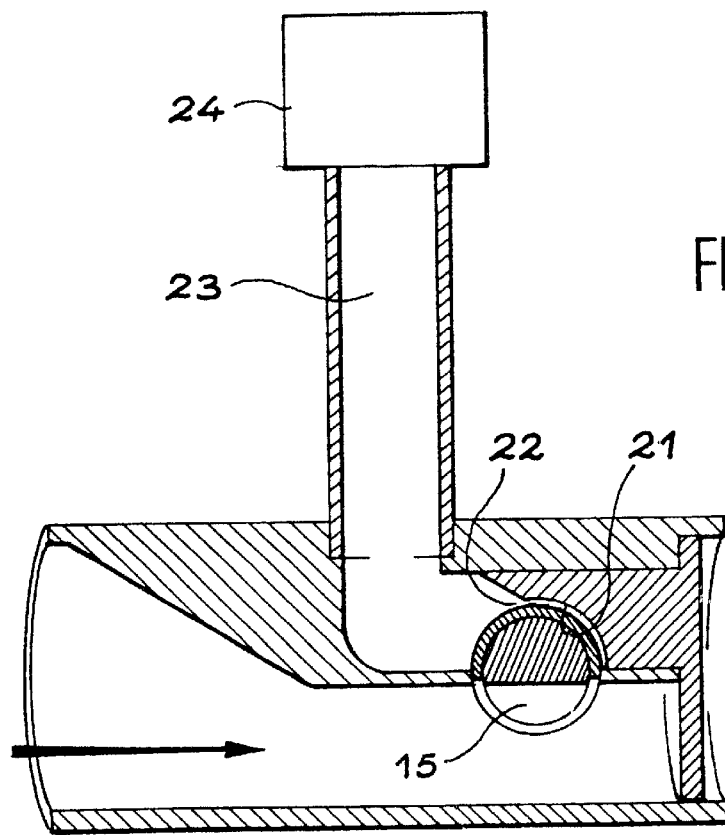
Figure 5:
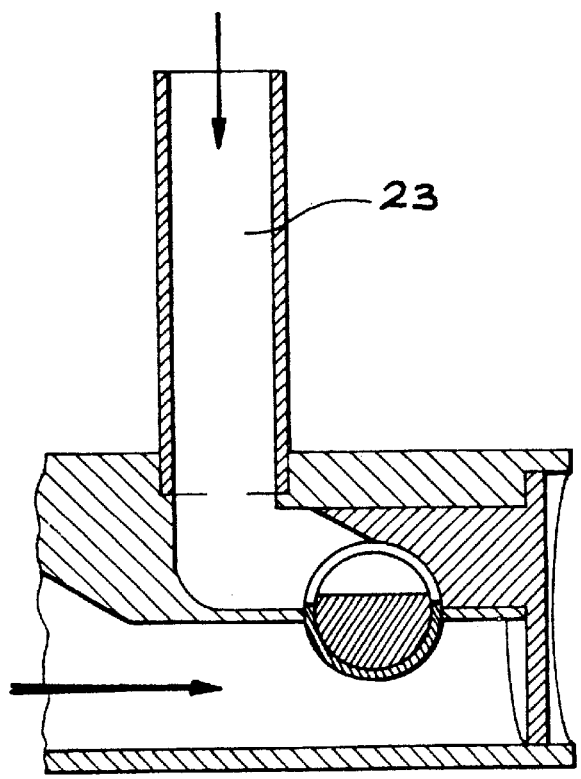
Figure 6:
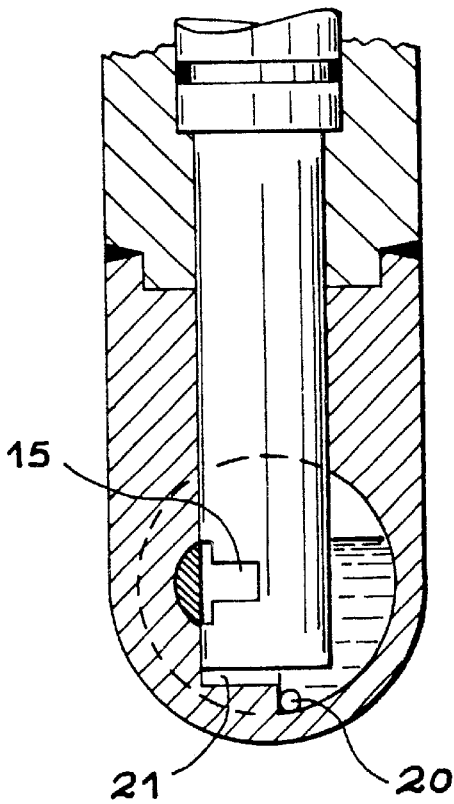
Figure 7:
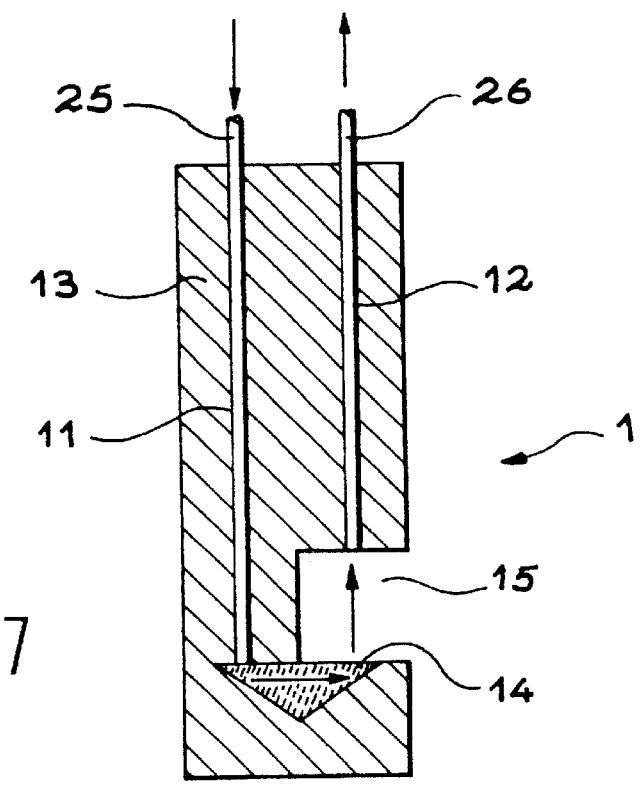
Figure 8:
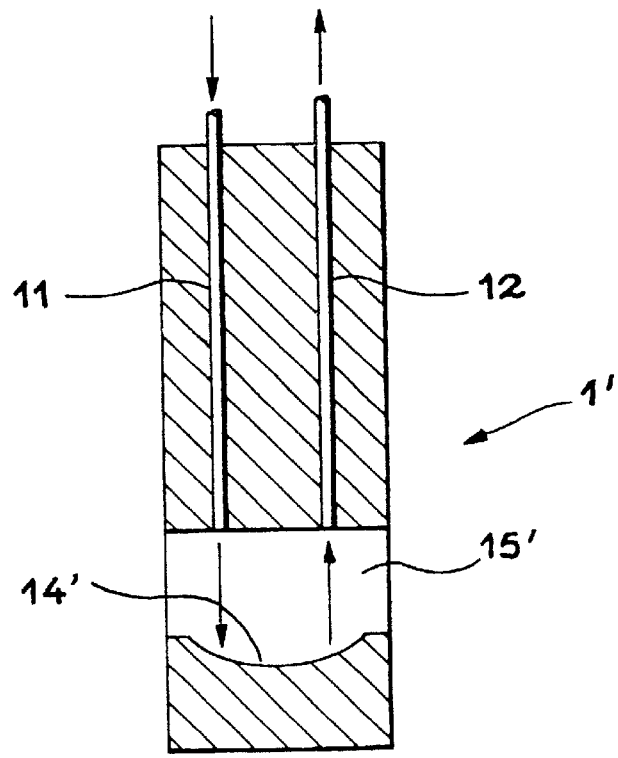

FIG. 3 is a view of the optode and of an adjacent portion of the flow circuit of the liquid, in longitudinal and vertical section of the circuit and probe, FIG. 4 shows the same part of the invention in horizontal section, FIG. 5 is identical to FIG. 4, except that the probe is in rinsing position instead of measuring position, FIG. 6 illustrates the same parts in cross section, FIGS. 7 and 8 illustrate two types of probes.

Figure 1:
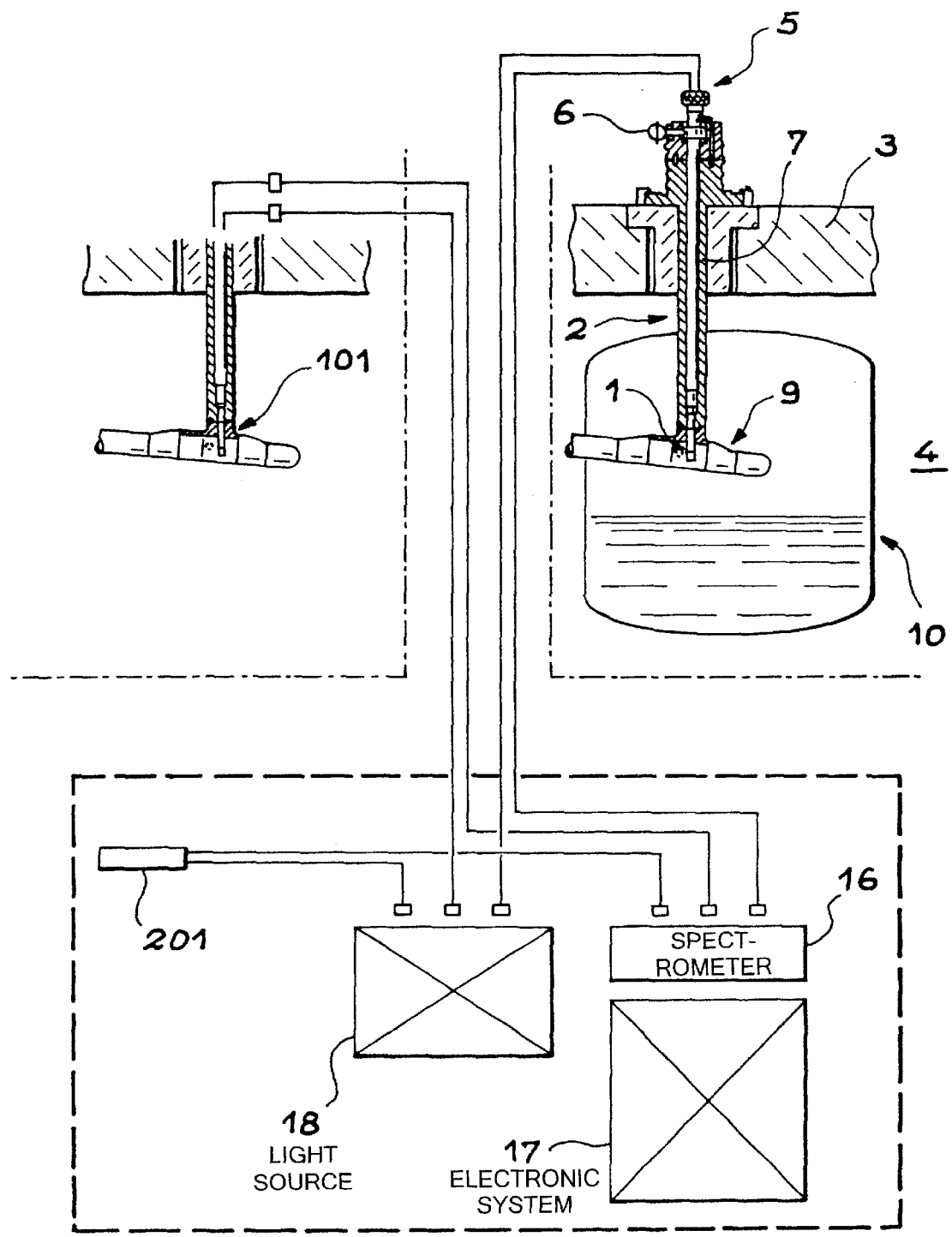
FIG. 1 illustrates the arrangement of the invention as a whole.
Figure 2:
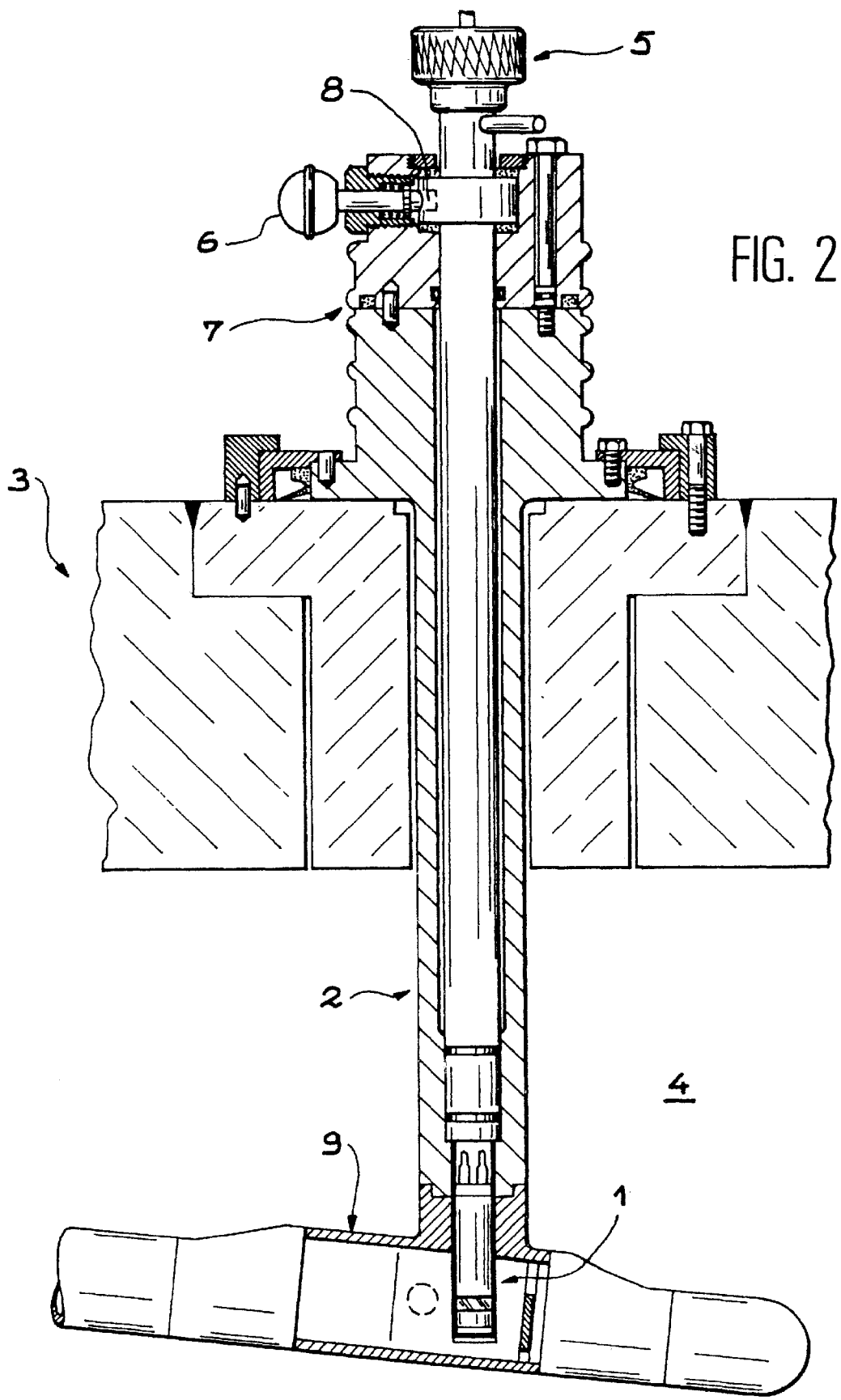
FIG. 2 illustrates the probe.

The measuring cell in FIG. 1 comprises an optode 1 as active part; it is placed at the end of probe 2, fully illustrated in FIG. 2, which passes through a protection slab 3 and whose end opposite optode 1, positioned outside a confined zone 4, carries a rotation command handle 5 for probe 2 in a protective jacket 7 which crosses though protection slab 3 and serves to house probe 2. A stop-pin 6 slides within jacket 7 perpendicular to probe 2, such as to be able to enter pierced holes 8 which the latter comprises and block its rotation; these pierced holes are two in number and diametrically opposite. Toric seals, not referenced, pressed between probe 2 and jacket 7, withhold any contamination under protection slab 3 within confined zone 4.

Optode 1 leads to a flow circuit or flow-pipe 9 of the liquid whose activity is to be measured. It may be a diversion branch of a major circuit into which a determined flow of liquid is diverted as required. Flow circuit 9 leads into a reservoir 10 into which runs the liquid to be measured, but it could also continue its route downstream and connect up with other circuit branches.

One possible composition of optode 1 is better visible in FIG. 7. Two branches 11 and 12 of an optic pathway cross through a black quartz block 13 (therefore fully opaque). A stainless steel envelope not shown surrounds optode 1, except in front of slit 15 which is described below to which it gives protection. Optic fibres 25 and 26 materialise branches 11 and 12 and are directed towards a prism 14 cut in the bottom of block 13 whose facets return the light from one branch 11 to the other 12. However, branch 11 extends as far as in front of prism 14, whereas branch 12 is separated from prism 14 by a slit 15 cut in block 13; the liquid to be measured fills this slit 15 and the light it emits is collected by branch 12 and measured by a spectrometer 16 shown in FIG. 1, then the measurement is processed by an electronic system 17 not shown in detail. Branch 11 is an outgoing branch used to calibrate optode 1 and is connected to a light source 18 which sends a well determined light intensity between measurements onto the active liquid. This light reaches spectrometer 16 after passing through prism 14, slit 15 and branch 12 which is a return branch. Spectrometer 16 and source 18 may be connected to several optodes at a time, conducting different measurements, via appropriate switches; one is shown and is denoted 101, another optode 201, connected in the same manner, is inactive and is only used for calibrating.

Another optode 1', in fact little different to the preceding one, may be used under the same conditions; it is shown in FIG. 8. Its slit 15' is longer than that of optode 1 and also extends as far as in front of the outgoing branch 11'. Also, prism 14 is replaced by a concave mirror 14' having similar reflective properties.

Attention is now turned to FIG. 3. Flow circuit 9 is tilted to guarantee permanent flow of the liquid, and its downstream opening is partly obstructed by a partition 19 which leaves the top part free and therefore forms an overflow barrier. The liquid fills flow circuit 9 until it reaches the top of overflow partition 19 and runs into reservoir 10. A lumen or discharge pierced outlet 20 is however provided at the bottom of the overflow partition 19; its purpose is to guarantee renewal of the liquid and to prevent it from stagnating in front of the overflow partition 19, which would harm measurement quality.

Optode 1 is immersed in flow circuit 9, its slit 15 being at the height of the overflow partition 19, so that it is fully immersed in the liquid to be measured.

FIG. 4 shows that optode 1 is in fact half housed in a semi-cylindrical alveolus 21 made in the wall of flow-pipe 9, such that it always has one surface exposed to the flow of liquid and one surface opposite this flow turned towards the surface of alveolus 21 from which it is separated by a clearance 22. Also, a rinsing duct 23 leads into alveolus 21. This rinsing duct slopes upwards as from alveolus 21 and leads to rinsing liquid supply means 24 not shown in detail and which may comprise a reservoir of the said liquid, closed by a gate and positioned on protection slab 23 in the zone accessible to operators.

The measuring cell may alternately be in a measuring state and a rinsing and calibrating state. In the former, optode 1 is placed as shown in FIGS. 3 and 4, slit 15 being turned towards flow circuit 9, and the liquid to be measured immerses optode 1 up to the height of the upper edge of the overflow partition 19, including at the site of clearance 22 and in the part corresponding to the rinsing duct 23. The liquid therefore occupies slit 15 and measurements are made in the usual manner. In the rinsing state, optode 1 is turned to place slit 15 facing the wall of alveolus 21 as shown in FIGS. 5 and 6, and rinsing liquid is poured into the rinsing circuit 23 where it flows under gravity following the slope of this circuit before by-passing optode 1 and passing into flow circuit 9 via clearance 22. The liquid to be measured is expelled from the vicinity of optode 1 by means of a slope of the rinsing circuit 23 that is more inclined than that of the flow circuit 9. The rinsing liquid therefore has a higher hydraulic load and crosses through slit 15 during this flow removing any impurities which may have lodged therein. It is seen that the rinsing operation is easily conducted since all that is required is to turn optode 1 and allow sufficient rinsing liquid to flow to expel the liquid to be measured that may have infiltrated the rinsing conduit 23 before conducting actual rinsing. It only requires a short interruption of measurement which can be subsequently resumed by replacing slit 15 in flow circuit 9; it suffices to wait until a new quantity of liquid to be measured has replaced the rinsing liquid. Since rinsing is carried out on the spot, it is not restrictive and may be repeated as soon as there is any doubt as to measurement quality; probe 2 is only removed under exceptional circumstances, for replacement in particular.

Calibration of probe 2 may advantageously be made at the end of rinsing, before it is returned to the measuring state. For this purpose a light source 18 is used as mentioned above.

We claim:

1. A liquid analysis cell for measuring the activity of a liquid, comprising a probe (2) fitted with one cylindrical measuring end (1), characterised in that the cell comprises a flow-pipe for the liquid provided with a cylindrical alveolus in which the cylindrical end of the probe is inserted, the alveolus (21) opening on one side into the pipe (9) and being delimited on the other side by a wall of said alveolus, a clearance (22) existing between the end (1) of the probe (2) and the wall, a rinsing liquid duct leading into the alveolus for supplying a rinsing liquid thereto via the wall, and in that the probe is mounted so that it can pivot freely within the cell so as to facilitate a cleaning action upon the probe by the rinsing liquid.

2. Measuring cell according to claim 1, characterised in that the rinsing liquid duct (23) slopes down from a rinsing liquid supply section (24) towards alveolus (21).

3. Measuring cell according to claim 2, characterised in that the rinsing liquid duct slopes downwards with a slope greater than a slope of the flow-pipe (9).

4. Measuring cell according to claim 1, characterised in that the flow-pipe comprises an opening limited by an overflow barrier (19) downstream from the alveolus.

5. Measuring cell according to claim 4, characterised in that the overflow barrier comprises a lower discharge pierced outlet (20).

* * * * *